(12) United States Patent
Steck et al.

(10) Patent No.: US 8,177,428 B2
(45) Date of Patent: May 15, 2012

(54) HOLDER DEVICE FOR DENTAL X-RAY DIGITAL SENSOR

(75) Inventors: John E. Steck, Round Lake, IL (US); Kimberly C. Brown, Huntly, IL (US); Nicole Sullivan, Elgin, IL (US)

(73) Assignee: DENTSPLY International Inc.

( * ) Notice: Subject to any disclaimer, the term of this patent is extended or adjusted under 35 U.S.C. 154(b) by 224 days.

(21) Appl. No.: 12/217,697

(22) Filed: Jul. 8, 2008

(65) Prior Publication Data
US 2010/0322386 A1 Dec. 23, 2010

(51) Int. Cl.
*A61B 6/14* (2006.01)
(52) U.S. Cl. ........................ 378/170; 378/168
(58) Field of Classification Search .................. 378/168, 378/169, 170
See application file for complete search history.

(56) References Cited

U.S. PATENT DOCUMENTS

| 3,473,026 | A  | 10/1969 | Updegrove |
| 5,677,537 | A  | 10/1997 | Pfeiffer |
| 6,203,195 | B1 | 3/2001  | Willis |
| 6,343,875 | B1 | 2/2002  | Eppinger et al. |
| 6,461,038 | B2 | 10/2002 | Pellegrini et al. |
| 6,592,256 | B2 | 7/2003  | Da Bold et al. |
| 6,652,141 | B1 | 11/2003 | Cianciosi |
| 6,905,244 | B2 | 6/2005  | Kilcher et al. |
| 7,226,208 | B2 | 6/2007  | Schmulenson |
| 2002/0196903 | A1 | 12/2002 | Eppinger |
| 2004/0096040 | A1 | 5/2004  | Kilcher et al. |

FOREIGN PATENT DOCUMENTS

| EP | 0397599 | 3/1994 |
| EP | 1623673 | 2/2006 |
| WO | WO 2007/022246 | 2/2007 |

OTHER PUBLICATIONS

Koch, Paul E., Snap Fit Design [online], (Sep. 2, 2003), [retrieved on Aug. 27, 2011], Retrieved from the Internet: <URL: http://web.archive.org/web/20030902170204/http://engr.bd.psu.edu/pkoch/plasticdesign/snap_design.htm>.*

* cited by examiner

*Primary Examiner* — Glen Kao
(74) *Attorney, Agent, or Firm* — Douglas J. Hura; David A. Zdurne; Leana Levin

(57) ABSTRACT

A sensor holder (10) includes a frame member (20) that bounds a void area (21) and which is configured to receive a sensor (11). A retaining means (50, 51) is provided to hold the sensor (11) to the frame (20) such that a connecting cable (12) affixed to the sensor (11) is secured and positioned by the void area (21) for a subsequent imaging procedure.

18 Claims, 7 Drawing Sheets

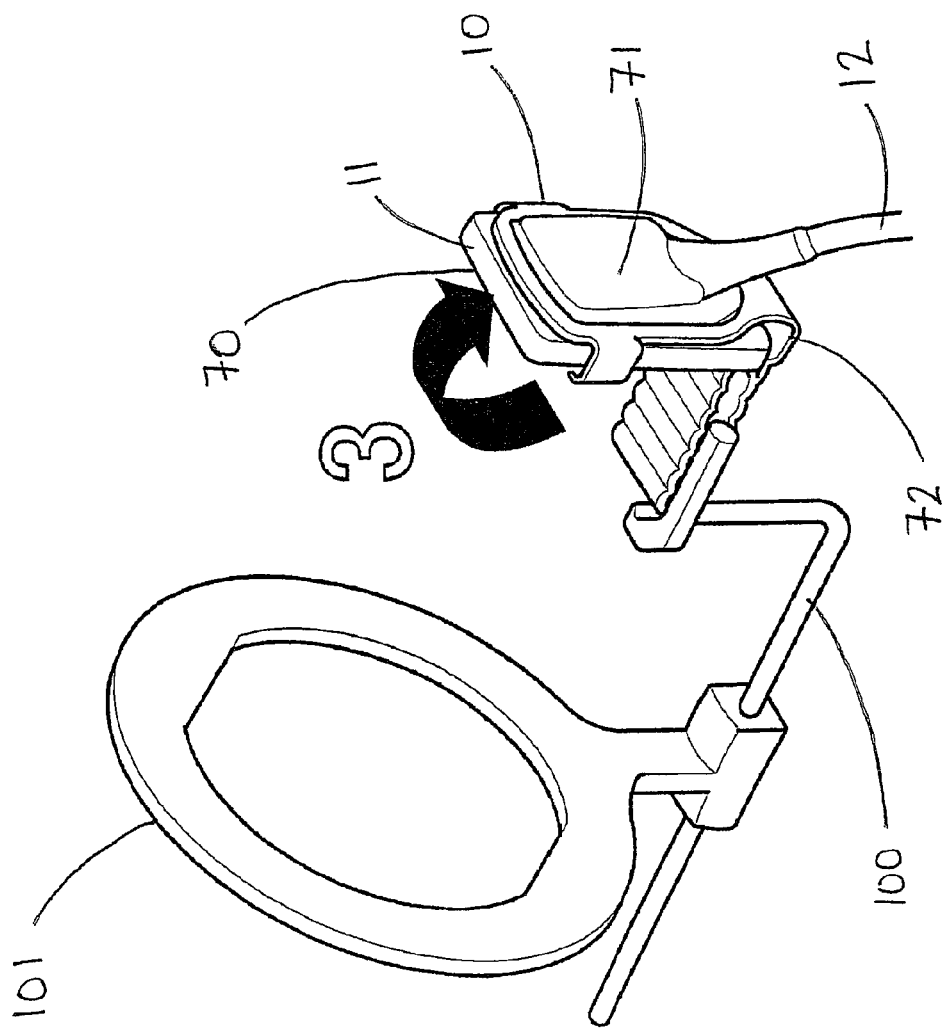

HOLDER DEVICE FOR DENTAL X-RAY DIGITAL SENSOR

TECHNICAL FIELD

A dental x-ray sensor holder is provided. The sensor holder has a geometry conducive to receive and secure a digital sensor of the type physically connected to another device such as a computer or the like via a connecting cable.

BACKGROUND OF THE INVENTION

Dental professionals have employed x-ray imaging for many years. A traditional dental x-ray procedure includes exposing an x-ray film to x-ray energy after it has passed through the target site. The film is developed and an image of the target site is achieved. It has also long been known that in order to obtain a useful image, the dental x-ray film must be positioned relative to the target site in a predetermined and secure manner. Many numbers of x-ray film holders and positioning devices have been developed, including for example, that shown in U.S. Pat. No. 3,473,026 which is hereby incorporated by reference for background purposes.

More recently, many dental professionals have used digital x-ray sensors in place of traditional x-ray films. An example of such a sensor is shown for example in U.S. Pat. No. 6,652,141 which is hereby incorporated by reference for background disclosure of x-ray sensors. As with x-ray films, it is necessary for the x-ray sensor to be secured in a predetermined position during the x-ray imaging procedure. In a manner similar to the use of x-ray films, holding and positioning devices have been developed for x-ray sensors.

A traditional problem with sensor holders is that connecting cable affixed to the sensor itself is cumbersome to position such that it does not interfere with the imaging procedure. Patient comfort is always a prime consideration in any dental procedure, and the positioning of the connecting cable is no different.

A need exists therefore, for a sensor holder than can be employed with digital sensor having a connecting cable. The holder should easily yet securely position and hold not only the sensor but also the connecting cable.

SUMMARY OF THE INVENTION

According to the present invention, a holder for a digital dental x-ray sensor of the type having a connecting cable is provided, wherein the holder comprises a bite block affixed to an upstanding frame. The frame is provided with at least one void area at least partially bound by said frame. The frame is further provided with a plurality of latch fingers configured to resiliently receive the sensor in a snap-fit relation so as to removeably secure the sensor to said frame. When a sensor is so secured in place by said latch fingers, the connecting cable is positioned through said void area.

There is also provided according to the invention method securing a digital dental x-ray sensor of the type having a connecting cable, comprising the steps of providing a holder as above, and inserting the sensor through said void area such that the sensor is positioned on one side of said frame while the connecting cable is positioned through said void area. The inventive method further includes if necessary, turning the sensor such that it is aligned with said latch fingers and snap-fitting the sensor to said frame and into a snap-fit receiving relation with said latch fingers.

BRIEF DESCRIPTION OF THE DRAWINGS

FIG. 7 is perspective view showing another exemplary step in removeably affixing a sensor to an inventive holder as in FIG. 5 and being sequential to the step of FIG. 6.

PREFERRED EMBODIMENTS FOR CARRYING OUT THE INVENTION

Figure 1:
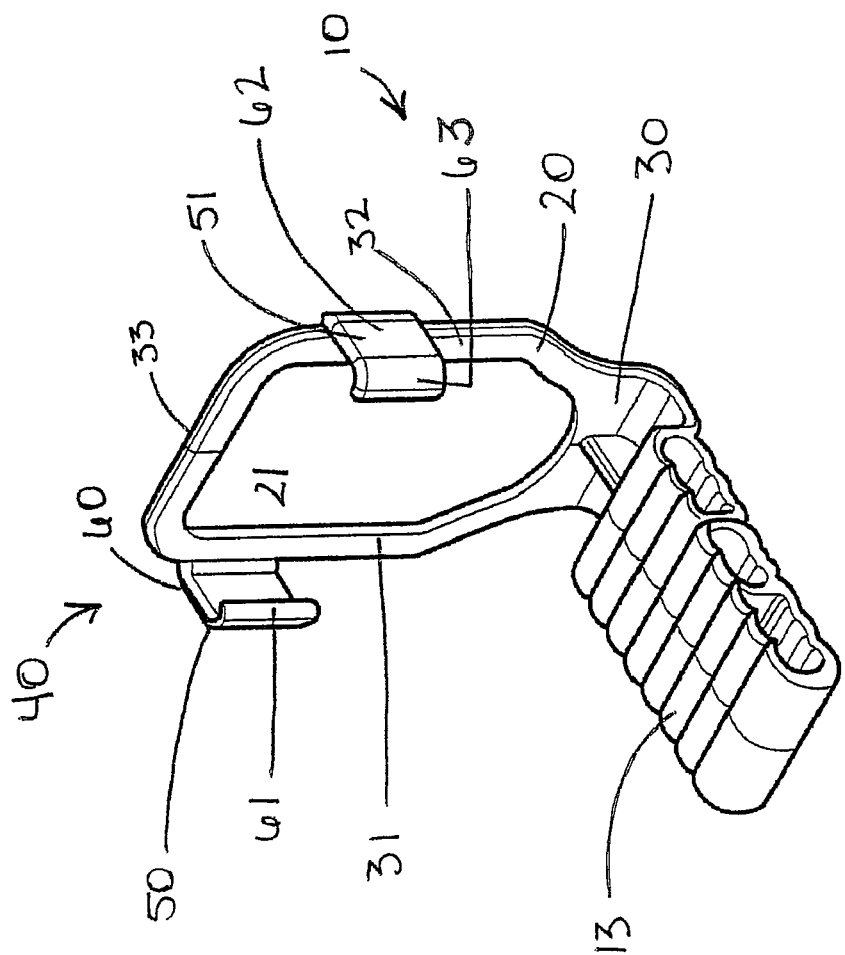
FIG. 1 is a perspective view of a sensor holder according to the concepts of the present invention, and configured for use particularly in anterior imaging procedures.

A sensor holder 10 according to the present invention is shown by way of example on the drawing figures and is generally designated by the number 10. While the invention has application to any digital dental sensor, holder 10 is particularly adapted for use with sensors of the type having connecting cable. For environmental purposes, an exemplary sensor is shown on the drawings (FIGS. 5-7) and is generally designated by the number 11. Sensor 11 is connected by an attached cable 12 to a peripheral device (not shown) of some kind, such as a computer or the like. Although the present invention has application to any shape or size of sensors, the invention is exemplified herein with reference to a sensor having a generally rectangular configuration, such shape being standard in the industry.

As is conventional in the art, holder 10 is preferably provided with a bite block 13 of any configuration. According to a unique aspect of the present invention, holder 10 is provided with an upstanding frame 20, preferably affixed to or formed contiguously with bite block 13. By "upstanding" it is meant that frame 20 is positioned at some angle to bite block 13. By nature, configuration and conventional function, bite block 13 will be held by a clamping action caused by the patient biting upon the bite block itself. Hence, when in use, the bite block 13 is at least somewhat parallel to the patient's occlusal plane (not shown). By being positioned at some angle with respect to the bite block and hence the occlusal plane, the upstanding frame is positioned to image either an upper or lower arch target site. An angle of about 90 degrees is often suitable although not necessarily a limitation of the present invention.

Frame 20 preferably bounds or delimits a void area 21. An exemplary frame 20 includes a base frame member 30 which is positioned proximate to bite block 13. Two spaced and opposed side frame members 31 and 32 extend from base frame member 30 and may be joined by a distal frame member 33. Preferably although not necessarily, frame members 30, 31, 32 and 33 lie in a similar plane.

At least one frame member carries a resilient latch finger 40. For example, side frame members 31 and 32 are shown to carry opposed latch fingers 50 and 51 respectively. By "resilient" it is meant that fingers 50 and 51 can move slightly with respect to their respective frame members in a resilient manner. By suitably selecting the material of manufacture, such as a plastic material, fingers 50 and 51 can be made to have such resiliency.

Further, fingers 50 and 51 are each provided with means to accept a sensor 11 in a snap-fit relation, and thereby to receive a sensor cooperatively therebetween. To facilitate such a snap-fit relation, an exemplary finger 50 is shown as having a base portion 60 and at least one curved portion 61 contiguous therewith. It is preferred though not necessary that base portion 60 and curved portion 61 be integrally formed with the rest of holder 10. Similarly, finger 51 has a base portion 62 and a curved portion 63. By "curved portion" it is meant that base portions 60 and 62 are positioned at some angle with respect to their respective curved portions 61 and 63. The angle can be sharp or curvilinear and can be any suitable angle. Preferably a pair of fingers 50 and 51 are positioned in an opposing spaced relation as discussed above, such that curved portions 61 and 63 are inwardly directed toward each other. Because fingers 50 and 51 are resilient, fingers 50 and 51 can receive a sensor 11 therebetween by slightly flexing and away from each other due to physical contact with the sensor 11. Once the sensor 11 has traveled sufficiently between fingers 50 and 51, curved portions 61 and 63 "close" upon sensor 11 and hold sensor 11 therebetween. Of course, any number of fingers such as fingers 50 and 51 can be employed. For example, it is possible that only one finger is used wherein it is carried by distal frame member 33; base frame member 30 may also carry a finger similar to finger 50 or 51; or all frame members may carry similar fingers (these embodiments not being shown). All such configurations are within the scope of the invention and are exemplified by the drawing figures.

Figure 5:
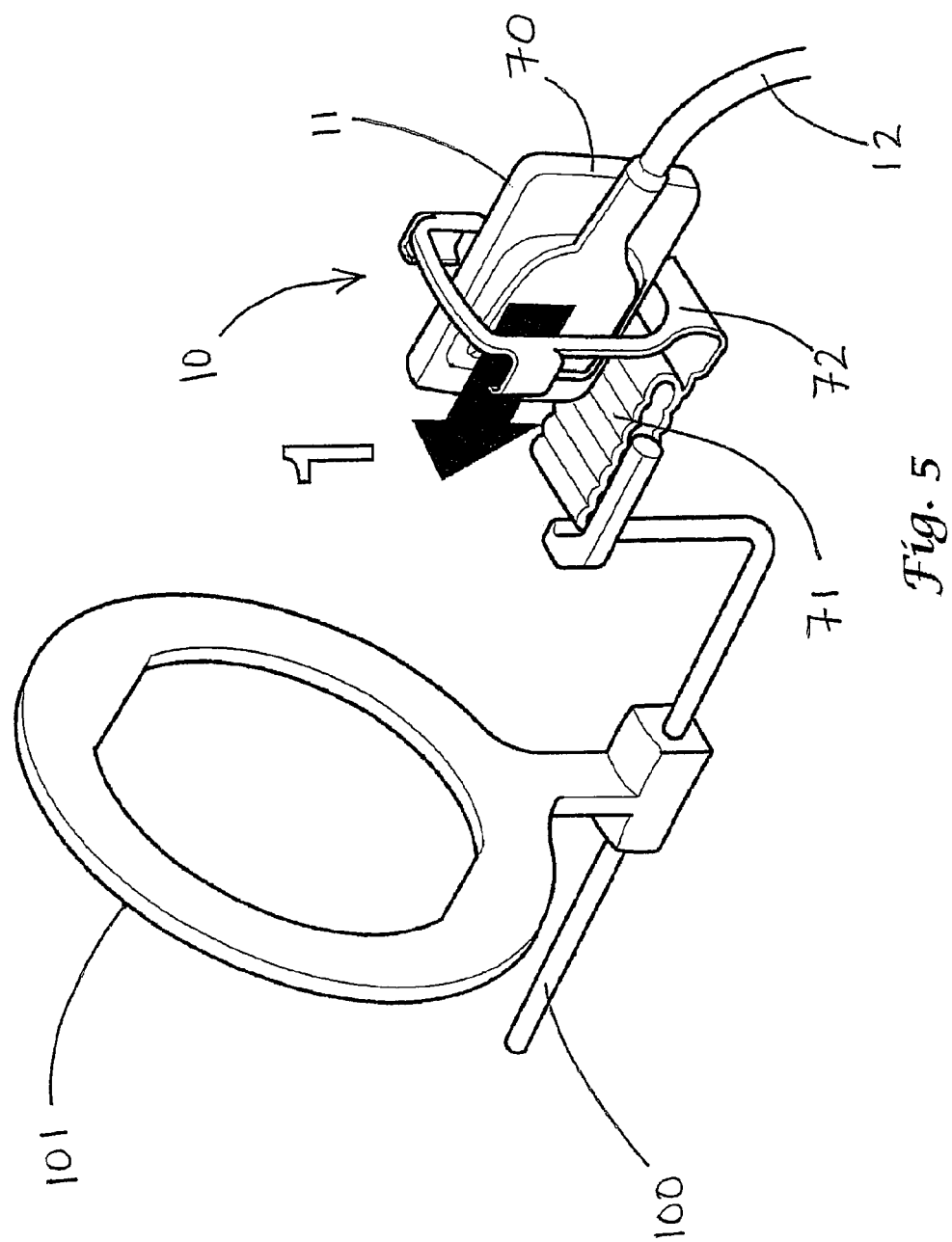
FIG. 5 is a perspective view showing an exemplary step in removeably affixing a sensor having a connecting cable to a sensor holder according to the present invention, and showing a support arm supporting both the inventive holder and a collimator ring for environmental purposes.
Figure 6:
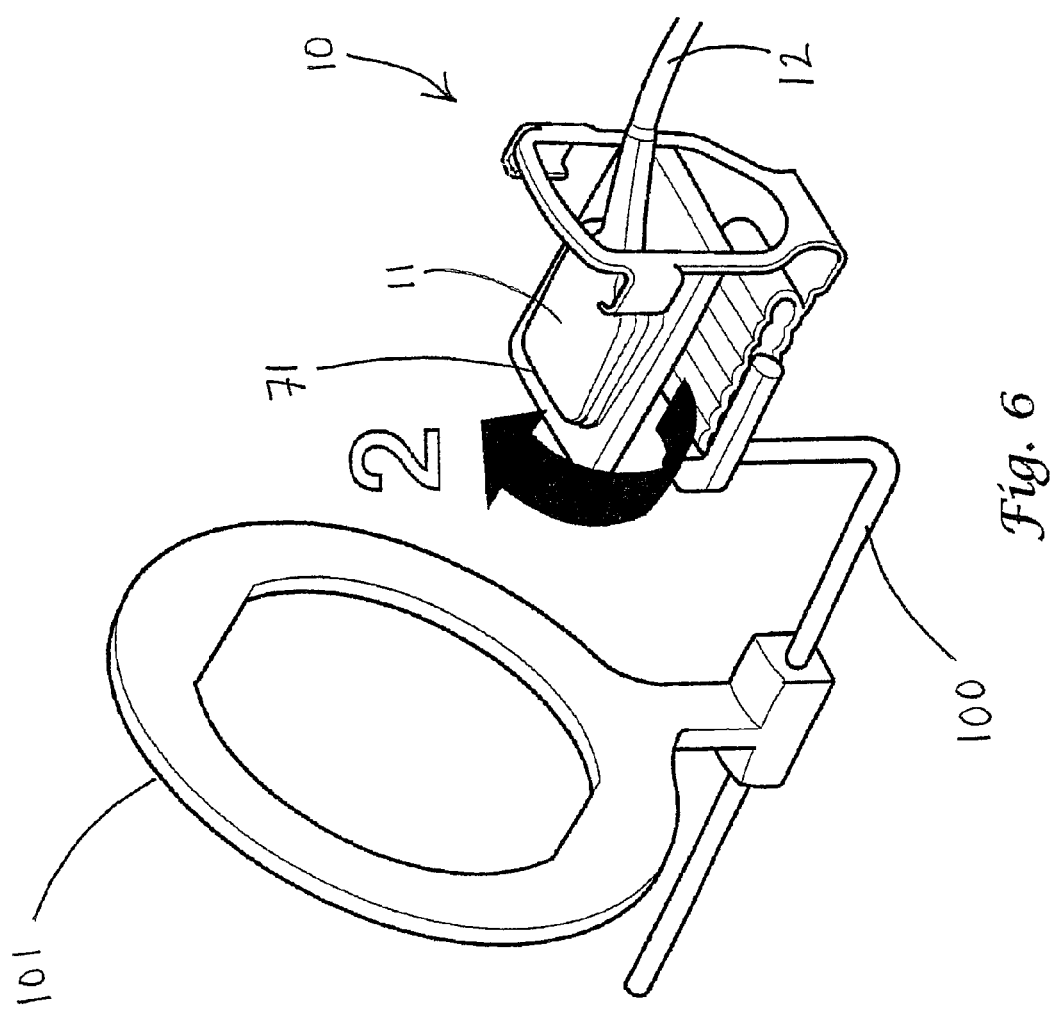
FIG. 6 is perspective view showing another exemplary step in removeably affixing a sensor to an inventive holder as in FIG. 5 and being sequential to the step of FIG. 5.

As stated above, frame 20 and its frame members such as frame members 30, 31, 32 and 33 preferably bound or delimit a void area 21. Although the invention is preferred and exemplified with a complete frame around void 21, it is not necessary that frame 20 completely surround void area 21 (this configuration not being shown but which will be understood). The inventive configuration of void 21 and frame 20 is such that when a sensor is so secured in place by said latch fingers, the connecting cable is positioned through said void area (FIGS. 5-7). According to the invention and a method thereof, a sensor 11 with a connecting cable 12 is inserted through frame 20 void area 21 from a side opposite the operational side of the holder 10 when sensor 11 is held therein for use. By "the operational side of the holder 10 when sensor 11 is held therein for use" it is meant that the sensor has a side 70 which is positioned to receive x-ray energy during an imaging procedure and a side 71 opposite side 70 which normally carries an attachment point 72 for cable 12. The side of sensor 11 that receives x-ray energy in use is the operational side of sensor 11. Hence, "the operational side of the holder 10 when sensor 11 is held therein for use" is the same side when sensor 11 is received and held in holder 10.

It will be appreciated that when sensor 11 is inserted through void area 21, cable 12 trails behind and through void area 21. At this point, sensor 11 can be turned an rotated if needed, such that it properly aligns with frame 20 and fingers 50 and 51 (FIGS. 6-7). It will also be appreciated that the steps of turning or rotating are not necessarily required. Once sensor 11 is properly aligned it is physically received by and snap-fit into place by fingers 50 and 51 as above described. It is to be appreciated that when sensor 11 is so positioned and held by holder 10, cable 12 is also secured and positioned by being held within void area 21. Thus the cable 12 is out of the way or at least in a known position for the patient and the dental professional during an imaging procedure.

For environmental purposes, holder 10 is shown in FIGS. 5-7 as being affixed to a support arm 100 and a collimator ring 101 as it would be in actual use during an imaging procedure.

Figure 3:
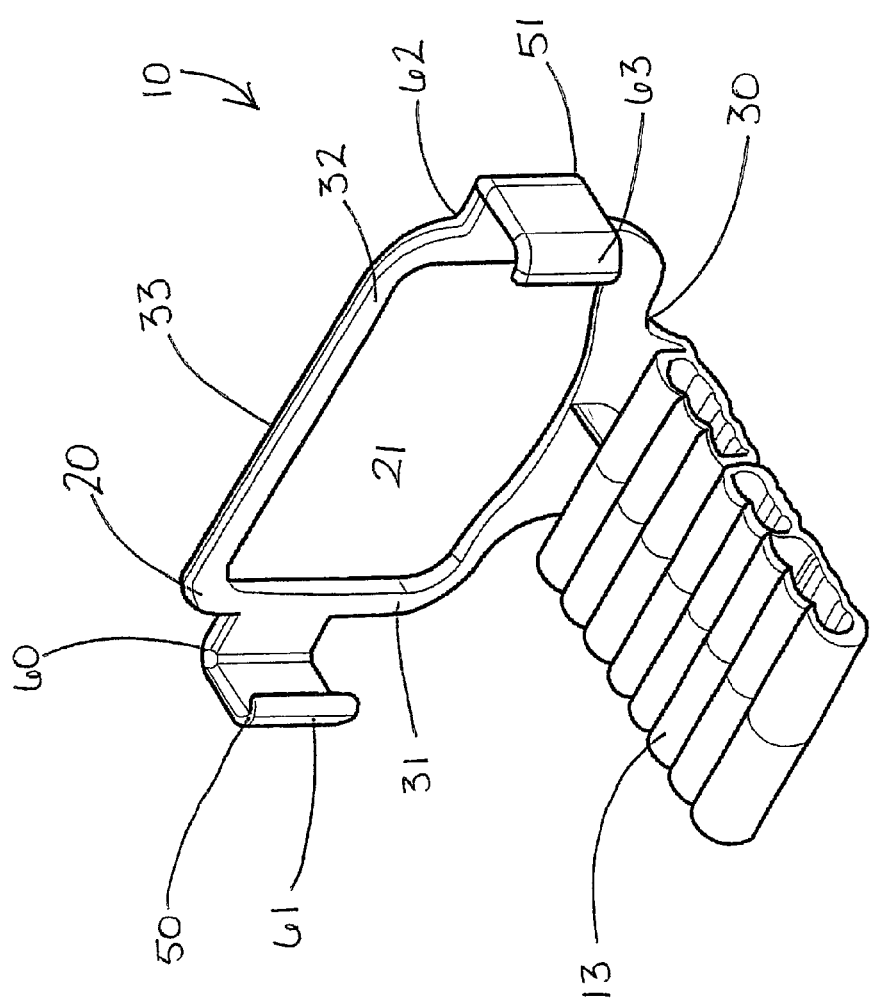
FIG. 3 is a perspective view of a sensor holder according to the concepts of the present invention, and configured for use particularly in posterior imaging procedures.
Figure 4:
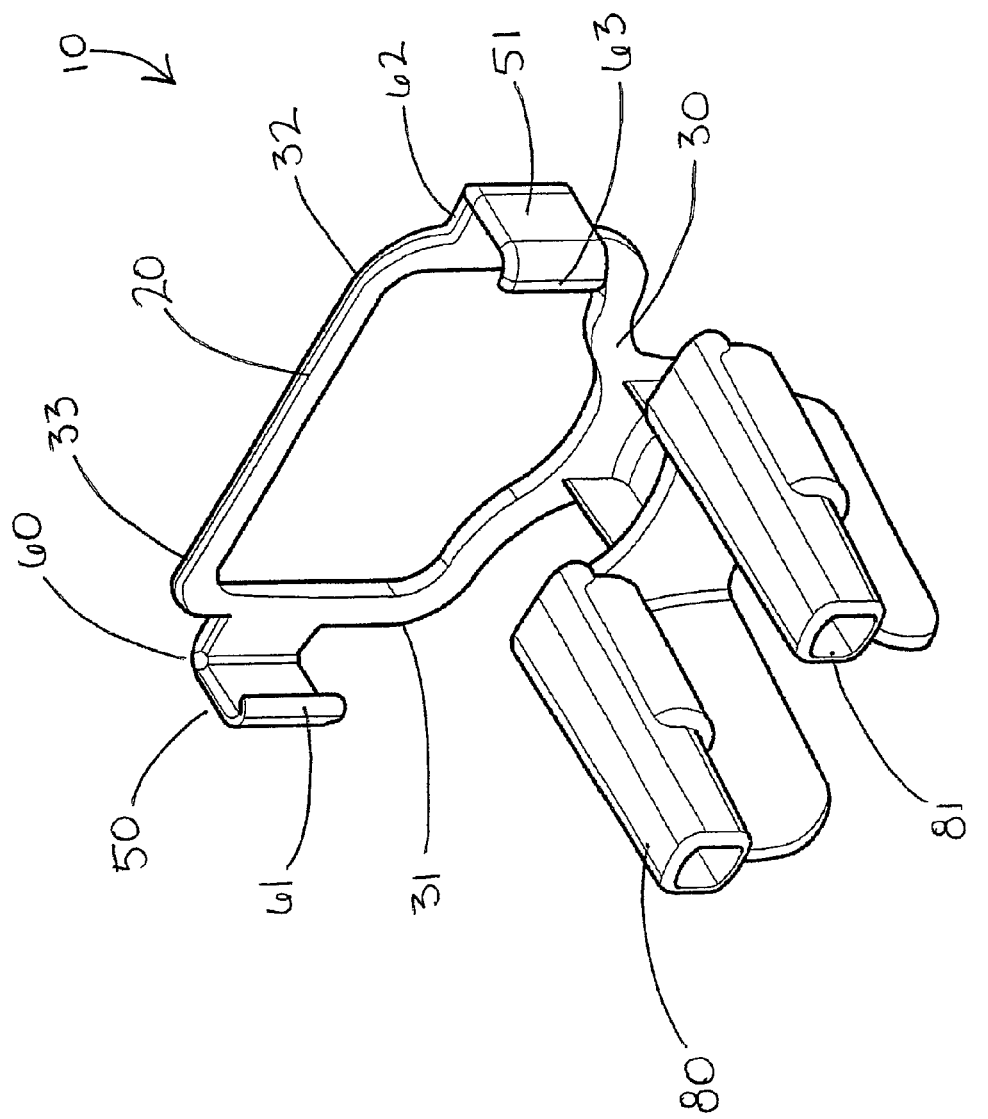
FIG. 4 is a perspective view of a sensor holder according to the concepts of the present invention, and configured for use particularly in endodontic imaging procedures.

FIGS. 1 and 3 show holders 10 suitable for use in imaging procedures for anterior and posterior positions respectively. FIG. 4 shows a holder 10 suitable for use in endodontic procedures wherein a bite block is formed by first and second spaced and opposing legs 80 and 81. The space between legs 80 and 81 allows the placement and use of endodontic equipment such as files during the imaging procedure.

Figure 2:
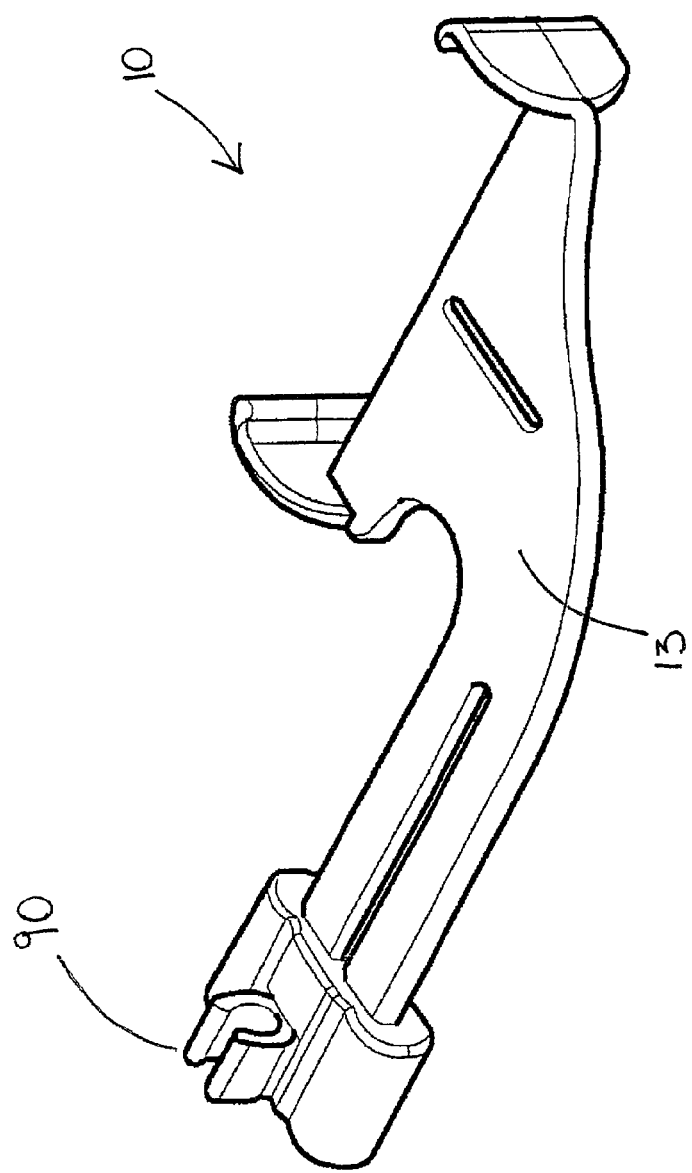
FIG. 2 is a perspective view of a sensor holder according to the concepts of the present invention, and configured for use particularly in bitewing imaging procedures.

FIG. 2 shows a bitewing holder 10 and which also has a cable conduit 90 positioned thereon. It will be appreciated that according to the invention, conduit 90 is useful to position and secure a cable 12 during imaging procedures.

It is evident therefore, that a sensor holder as shown and described carries out the intended purpose of the invention and otherwise provides a valuable contribution and advance to the art of sensor holders. The invention and its various embodiments have been exemplified herein by description and drawings without attempting to show all embodiments and variations that are all within the scope of the invention. Thus the actual scope of the invention shall be limited only by the attached claims.

The invention claimed is:

1. A dental system comprising:
    a digital dental x-ray sensor having a connecting cable; and
    a holder for the digital dental x-ray sensor, the holder including:
        a bite block affixed to an upstanding frame, said frame provided with at least one void area completely bound by said frame; said frame further provided with a plurality of latch fingers configured to resiliently receive the digital dental x-ray sensor in a snap-fit relation so as to removeably secure the sensor to said frame; such that when the digital dental x-ray sensor is so secured in place by said latch fingers, the connecting cable is positioned through said void area;
        wherein the void area being completely bound by the frame is dimensioned such to allow the sensor to pass therethrough.

2. The holder of claim 1, wherein the frame includes a plurality of frame members such that the plurality of latch fingers move slightly with respect to their respective frame members in a resilient manner.

3. The holder of claim 2, wherein the plurality of latch fingers are each provided with means to accept the sensor in a snap-fit relation, and thereby to receive a sensor cooperatively therebetween.

4. The holder of claim 2, wherein the latch fingers receive the sensor therebetween by slightly flexing and away from each other due to physical contact with the sensor.

5. The holder of claim 1, wherein the plurality of latch fingers extend generally perpendicularly from the frame.

6. The holder of claim 1, wherein the space between the plurality of latch fingers is dimensioned such to allow at least a portion of the sensor to pass therethrough.

7. The holder of claim 1, wherein the void area extends through the frame along an axis generally parallel to the plurality of latch fingers extending from the frame.

8. The holder of claim 1, wherein:
    i) the frame includes a plurality of frame members such that the plurality of latch fingers move slightly with respect to their respective frame members in a resilient manner;

ii) the plurality of latch fingers receive the sensor therebetween by slightly flexing and away from each other due to physical contact with the sensor; and iii) the space between the plurality of latch fingers is dimensioned such to allow at least a portion of the sensor to pass therethrough.

9. A method securing a digital dental x-ray sensor of the type having a connecting cable, comprising the steps of:

providing a digital dental x-ray sensor having a connecting cable;

providing a holder comprising a bite block affixed to an upstanding frame, said frame provided with at least one void area completely bound by said frame; said frame further provided with a plurality of latch fingers configured to resiliently receive the digital dental x-ray sensor in a snap-fit relation so as to removeably secure the digital dental x-ray sensor to said frame, wherein the void area being completely bound by the frame is dimensioned such to allow the sensor to pass therethrough;

inserting the digital dental x-ray sensor through said void area such that the sensor is positioned on one side of said frame while the connecting cable is positioned through said void area;

when necessary turning the sensor such that the sensor is aligned with said latch fingers; and snap-fitting the sensor to said frame and into a snap-fit receiving relation with said latch fingers.

10. The method of claim 9, wherein the frame includes a plurality of frame members such that the plurality of latch fingers move slightly with respect to their respective frame members in a resilient manner.

11. The method of claim 10, wherein the plurality of latch fingers are each provided with means to accept the sensor in a snap-fit relation, and thereby to receive a sensor cooperatively therebetween.

12. The method of claim 10, wherein the plurality of latch fingers receive the sensor therebetween by slightly flexing and away from each other due to physical contact with the sensor.

13. The method of claim 9, wherein the plurality of latch fingers extend generally perpendicularly from the frame.

14. The method of claim 9, wherein the space between the plurality of latch fingers is dimensioned such to allow at least a portion of the sensor to pass therethrough.

15. The method of claim 9, wherein:

i) the frame includes a plurality of frame members such that the plurality of latch fingers move slightly with respect to their respective frame members in a resilient manner;

ii) the plurality of latch fingers receive the sensor therebetween by slightly flexing and away from each other due to physical contact with the sensor; and iii) the space between the plurality of latch fingers is dimensioned such to allow at least a portion of the sensor to pass therethrough.

16. The method of claim 9, wherein the void area extends through the frame along an axis generally parallel to the plurality of latch fingers extending from the frame.

17. The method of claim 9, wherein the sensor is inserted through said void area and then rotated to align the sensor for being received by the plurality of latch fingers.

18. The method of claim 17, wherein after the sensor is snap-fitted to the frame, a potion of the connecting cable remains extended through the void area.

\* \* \* \* \*